United States Patent
Hirano et al.

(10) Patent No.: US 9,212,267 B2
(45) Date of Patent: Dec. 15, 2015

(54) METHOD OF PRODUCING METAL COMPLEX-SUPPORTING MESOPOROUS MATERIAL

(71) Applicants: Tokyo Ohka Kogyo Co., Ltd., Kawasaki-shi (JP); Tokyo Institute of Technology, Tokyo (JP)

(72) Inventors: Isao Hirano, Kawasaki (JP); Takane Imaoka, Tokyo (JP); Kimihisa Yamamoto, Tokyo (JP)

(73) Assignees: TOKYO OHKA KOGYO CO., LTD., Kawasaki-Shi (JP); TOKYO INSTITUTE OF TECHNOLOGY, Tokyo (JP)

( * ) Notice: Subject to any disclaimer, the term of this patent is extended or adjusted under 35 U.S.C. 154(b) by 112 days.

(21) Appl. No.: 14/188,119

(22) Filed: Feb. 24, 2014

(65) Prior Publication Data

US 2014/0242388 A1    Aug. 28, 2014

(30) Foreign Application Priority Data

Feb. 27, 2013    (JP) ................................ 2013-037927

(51) Int. Cl.
*C08J 5/00*    (2006.01)
*C08G 83/00*    (2006.01)

(52) U.S. Cl.
CPC ................ *C08J 5/00* (2013.01); *C08G 83/003* (2013.01); *C08J 2379/00* (2013.01); *Y10T 428/2991* (2015.01)

(58) Field of Classification Search
CPC ...... C08J 5/00; C08J 2379/00; C08G 83/003; Y10T 428/2991
USPC ......... 428/403; 252/182.3, 301.4 F; 502/300, 502/344, 355
See application file for complete search history.

(56) References Cited

U.S. PATENT DOCUMENTS

| 2003/0174638 | A1* | 9/2003 | Maekawa et al. | 369/275.1 |
| 2012/0308470 | A1* | 12/2012 | Ono et al. | 423/447.1 |
| 2013/0040107 | A1* | 2/2013 | Hirano et al. | 428/143 |
| 2014/0242388 | A1* | 8/2014 | Hirano et al. | 428/403 |

FOREIGN PATENT DOCUMENTS

| JP | 2001-508484 | * | 6/2011 |
| WO | WO 98/30604 | | 7/1998 |
| WO | WO98/30604 | * | 7/1998 |

OTHER PUBLICATIONS

Imaoka et al, "Stabilization of Catalyst by Supporitng Sub-Nano Platinum Cluster Encapsulated in Dendrimer" Sep. 14, 2012, p. 470.*
Yamamoto et al, "Size Specific Catalytic activity of Platinum Clusters Enhances oxygen Reduction Reactions" Nature Chemistry, vol. 1, pp. 397-402, Aug. 2009.*
Imaoka et al., "Stabilization of Catalyst by Supporting Sub-Nano Platinum Cluster Encapsulated in Dendrimer," Sep. 14, 2012, p. 470.
Yamamoto et al., "Size Specific Catalytic Activity of Platinum Clusters Enhances Oxygen Reduction Reactions," Nature Chemistry, vol. 1, pp. 397-402, Aug. 2009.

* cited by examiner

*Primary Examiner* — Leszek Kiliman
(74) *Attorney, Agent, or Firm* — Knobbe, Martens, Olson & Bear, LLP

(57) ABSTRACT

A method of producing a metal complex-supporting mesoporous material that can support a metal complex in the pores thereof without causing aggregation of the metal complex. A metal complex-supporting mesoporous material supporting a metal complex in the pores thereof without causing aggregation of the metal complex. A method of producing a mesoporous material supporting metal-containing nanoparticles using the metal complex supported in the pores of the mesoporous material as a template. A solution of a metal complex prepared by a phenyl azomethine dendrimer compound having a specific structure is brought into contact with a mesoporous material so that the metal complex of the phenyl azomethine dendrimer compound is supported by the mesoporous material.

7 Claims, 6 Drawing Sheets

METHOD OF PRODUCING METAL COMPLEX-SUPPORTING MESOPOROUS MATERIAL

This application claims priority under 35 U.S.C. §119(a)-(d) to Japanese Patent Application No. 2013-037927, filed Feb. 27, 2013, the content of which is incorporated herein by reference.

BACKGROUND OF THE INVENTION

1. Field of the Invention

The present invention relates to a method of producing a metal complex-supporting mesoporous material, a metal complex-supporting mesoporous material, and a method of producing a mesoporous material supporting metal-containing nanoparticles using the metal complex-supporting mesoporous material.

2. Related Art

In recent years, metal nanoparticles or nanoparticles of metal-containing compounds have attracted attention as basic materials for use in medical drugs, electronically functional materials, environmentally compatible materials and the like. Metal-containing nanoparticles are fine particles having a diameter of typically no greater than 10 nm, and they are not only useful per se as medical drugs, electronic function materials, environmentally compatible materials and the like, but also superior in activities as a catalyst for synthesizing the same. Such characteristic features result from a quantum effect due to the nanoparticles being fine particles having a diameter of no greater than 10 nm, and a greater active surface area accompanied by being fine particles. However, preparation of metal-containing nanoparticles having a diameter of no greater than 10 nm is difficult, in general, since an agglutinative action among the particles increases along with the extent of micronization.

Under such circumstances, as methods for producing metal-containing nanoparticles, methods in which a dendrimer compound is used as a template have been proposed (see, for example, Patent Document 1). Dendrimer compounds that include in the backbone a nitrogen atom, etc., having an unpaired electron pair are capable of forming a complex with a Lewis acid, and can incorporate a variety of molecules and atoms within their molecules.

For example, in a known method, a complex composed of a dendrimer compound called TPM-G4 and $PtCl_4$ is reduced with sodium borohydride in a solution to prepare a dendrimer compound encapsulating Pt nanoparticles, and the dendrimer compound encapsulating Pt nanoparticles is then supported in pores of mesoporous carbon (see Non-Patent Document 1). The dendrimer compound called TPM-G4 is described in Non-Patent Document 2.

If the method described in Non-Patent Document 1 is applied to a method of producing metal-containing nanoparticles using a dendrimer compound as a template, mesoporous carbon supporting Pt nanoparticles can be prepared by removing the dendrimer compound from mesoporous carbon supporting the dendrimer compound encapsulating Pt nanoparticles.

[Patent Document 1] Japanese Unexamined Patent Application (Translation of PCT Application), Publication No. 2001-508484

[Non-Patent Document 1] Takane Imaoka, Yushi Hongo, Wang Jae Chun, and Kimihisa Yamamoto, "Stabilization of catalyst by supporting sub-nano platinum cluster encapsulated in dendrimer", The 110th Catalyst Forum A Proceeding, Sep. 14, 2012, p. 470

[Non-Patent Document 2] K. Yamamoto, T. Imaoka, W. Chun, O. Enoki, H. Katoh, M. Takenaga, and A. Sonoi, Nature Chem., 1, 397, 2009

SUMMARY OF THE INVENTION

In the method described in Non-Patent Document 1, however, in the process for preparing a dendrimer compound encapsulating Pt nanoparticles by reducing a complex composed of a dendrimer compound, TPM-G4, and $PtCl_4$ with sodium borohydride in a solution, aggregation of the dendrimer compound encapsulating Pt nanoparticles occurs. The aggregation of the dendrimer compound encapsulating Pt nanoparticles causes problems, depending on the pore size of the mesoporous carbon, that the aggregates of the dendrimer compound encapsulating Pt nanoparticles are supported in the pores of mesoporous carbon or that the dendrimer compound encapsulating Pt nanoparticles cannot be efficiently incorporated into the pores of mesoporous carbon.

As a method for avoiding such problems, it is proposed to support the complex composed of TPM-G4 and $PtCl_4$ in the pores and then reduce the complex composed of TPM-G4 and $PtCl_4$. However, whether a compound is supported in the pores of a mesoporous material is highly affected not only by the size of the compound but also by the affinity between the compound and the surface of the mesoporous material. In addition, it is known in various complexes that a ligand and its complex highly differ in affinity to a hydrophobic surface or a hydrophilic surface.

Under such circumstances, despite of the fact that a dendrimer compound encapsulating Pt nanoparticles can be supported in the pores of mesoporous carbon, it is difficult even for those skilled in the art to predict that the complex composed of TPM-G4 and $PtCl_4$ is supported in the pores of mesoporous carbon.

The present invention was made in view of the above problems, and an object of the present invention is to provide a method of producing a metal complex-supporting mesoporous material that can support a metal complex in the pores of the mesoporous material without causing aggregation of the metal complex. Another object of the present invention is to provide a metal complex-supporting mesoporous material in which a metal complex is supported in the pores of the mesoporous material without aggregating. Another object of the present invention is to provide a method of producing a mesoporous material supporting metal-containing nanoparticles using the metal complex supported in the pores of the mesoporous material as a template.

The present inventors have found that the above problems can be solved by bringing a solution of a metal complex formed using a phenyl azomethine dendrimer compound having a specific structure into contact with a mesoporous material and thereby supporting the metal complex of the phenyl azomethine dendrimer compound by the mesoporous material, and have completed the present invention.

A first embodiment of the present invention relates to a method of producing a metal complex-supporting mesoporous material. The method includes a step of bringing a solution containing a metal complex of a phenyl azomethine dendrimer compound represented by the following Formula (1) coordinated with a metal element into contact with a mesoporous material.

$$AB_nR_m \quad (1)$$

wherein A in the above general formula (1) is a core molecular group of the phenyl azomethine dendrimer and represented by a structure of the following formula:

wherein R¹ represents an aromatic group that may have a substituent, and p represents the number of bonds to the R¹; and B in the above general formula (1) is represented by a structure of the following formula:

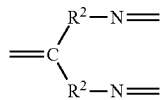

in which one azomethine bond is formed for the A, the $R^2$ represents an aromatic group that may have the same or different substituent;

the R in the above general formula (1) is represented by a structure of the following formula:

in which an azomethine bond is formed to the B as a terminal group, and the $R^3$ represents an aromatic group that may have the same or different substituent;

n represents a generation number through a structure of the B of the phenyl azomethine dendrimer; and m represents the number of terminal groups R of the phenyl azomethine dendrimer, m=p when n=0, and m=$2^n$p when n≥1.

A second embodiment of the present invention relates to a metal complex-supporting mesoporous material supporting a metal complex of a phenyl azomethine dendrimer compound represented by Formula (1) coordinated with a metal element.

A third embodiment of the present invention relates to a method of producing a mesoporous material supporting metal-containing nanoparticles. The method includes a step of converting the metal complex in the metal complex-supporting mesoporous material according to the second embodiment into a phenyl azomethine dendrimer compound encapsulating metal-containing nanoparticles and then removing the phenyl azomethine dendrimer compound from the mesoporous material.

The present invention can provide a method of producing a metal complex-supporting mesoporous material that can support a metal complex in the pores of the mesoporous material without causing aggregation of the metal complex and a metal complex-supporting mesoporous material produced by the method. The present invention can also provide a method of producing a mesoporous material supporting metal-containing nanoparticles using the metal complex supported in the pores of the mesoporous material prepared by the above-mentioned method as a template.

DETAILED DESCRIPTION OF THE INVENTION

Figure 1:
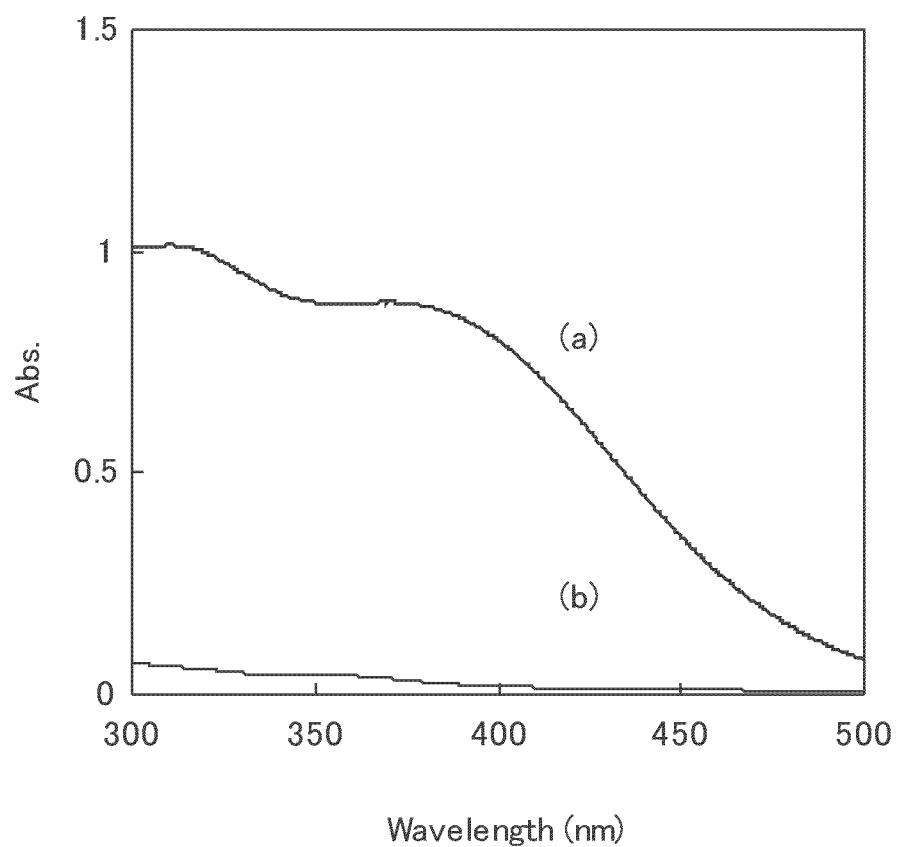
FIG. 1 is a graph showing absorption spectra of a solution of a DPAG4er-AuCl₃ complex and the solution of the DPAG4er-AuCl₃ complex to which mesoporous silica was added, prepared in Example 1.

Method of Producing Metal Complex-Supporting Mesoporous Material

The method of producing a metal complex-supporting mesoporous material includes a step of bringing a solution containing a metal complex of a phenyl azomethine dendrimer compound represented by Formula (1) coordinated with a metal element into contact with a mesoporous material. The solution containing a metal complex of a phenyl azomethine dendrimer compound, the mesoporous material, and a method of supporting the metal complex by the mesoporous material will now be described.

Solution of Metal Complex of Phenyl Azomethine Dendrimer Compound

The metal complex of a phenyl azomethine dendrimer compound can be prepared by mixing a phenyl azomethine dendrimer compound represented by Formula (1) and a metal compound containing a metal element in a solution.

A in the above general formula (1) is a core molecular group of the phenyl azomethine dendrimer compound, and the phenyl azomethine dendrimer molecule grows a linkage of unit represented by B in general formula (1) to the outer side from the core molecular group as a center. As a result, the phenyl azomethine dendrimer molecule after growth has a structure in which the B is linked and radially grown from the A as a center. The number that B and R (to be described later) are linked refers to the "generation", the generation adjacent to the core molecular group A is a first generation, and the generation number increases toward the outer side. A in the above general formula (1) is represented by a structure of the following formula:

and R¹ represents an aromatic group that may have a substituent, p represents the number of bonds to R¹.

B in the above general formula (1) is represented by a structure of the following formula:

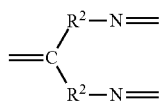

in which one azomethine bond is formed for the A, and $R^2$ represents an aromatic group that may have the same or different substituent. B constitutes the generation of the phenyl azomethine dendrimer molecule, and B which is directly bound to the core molecular group A becomes a first generation.

R in the above general formula (1) is represented by a structure of the following formula:

in which an azomethine bond is formed to B as a terminal group, and $R^3$ represents an aromatic group that may have the same or different substituent. R is positioned at a terminal of a structure in which the phenyl azomethine dendrimer molecule is radially grown, and constitutes a generation similarly to B described above.

In the above general formula (1), n represents the generation number through a structure of B of the phenyl azomethine dendrimer, m represents the number of terminal groups R of the phenyl azomethine dendrimer, m=p when n=0, and m=$2^n$p when n≥1.

Each of $R^1$, $R^2$ and $R^3$, which are an aromatic group that may have a substituent, may be independently a phenyl group or a similar structure thereof as a backbone structure, and examples thereof include various groups, such as a phenyl group, a biphenyl group, a biphenyl alkylene group, a biphenyl oxy group, a biphenyl carbonyl group, a phenyl alkyl group and the like. In these backbones, as a substituent, a halogen atom such as a chlorine atom, a bromine atom, a fluorine atom and the like, an alkyl group such as a methyl group, an ethyl group and the like, a haloalkyl group such as a chloromethyl group, a trifluoromethyl group and the like, an alkoxy group such as a methoxy group, an ethoxy group and the like, an alkoxyalkyl group such as a methoxyethyl group and the like, various substituents, such as an alkylthio group, a carbonyl group, a cyano group, an amino group, a nitro group and the like are exemplified. The backbone may have any one or a plurality of these substituents.

Among the substituents, a substituent having high electron donating property, such as a methoxy group and an amino group, or a substituent having high electron accepting property, such as a cyano group and a carbonyl group, is preferred.

In the core portion represented by the formula $R^1(-N=)_p$, p is not particularly limited, but may be, for example, an integer of from 1 to 4. Furthermore, the n in the above general formula (1) is an integer of 0 or 1 or more, but for example, 2 to 6 is preferably exemplified.

One form of the phenyl azomethine dendrimer compound may be a compound represented by the following formula. The compound represented by the following formula is a phenyl azomethine dendrimer compound having a generation number of 4.

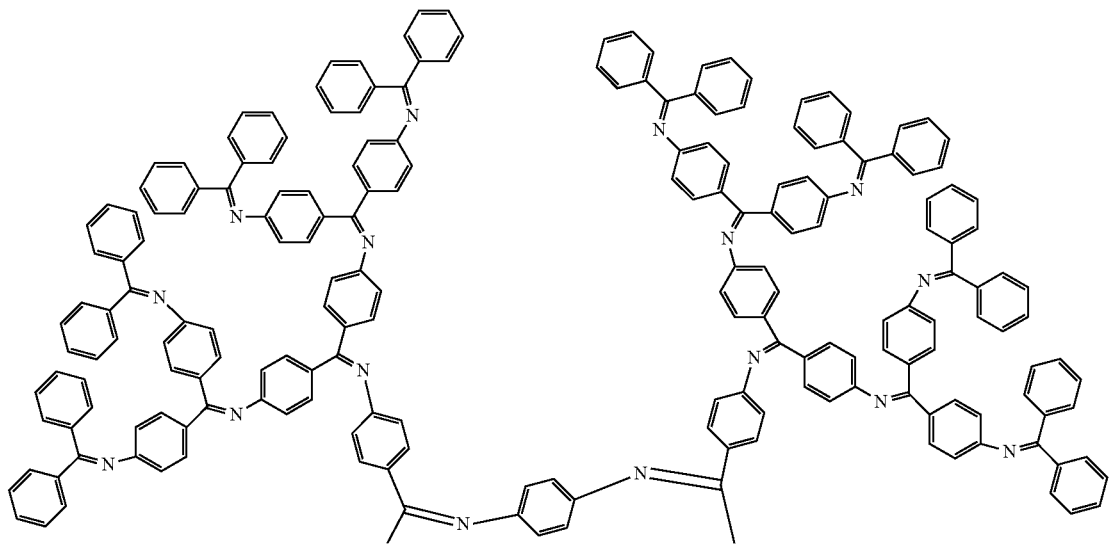

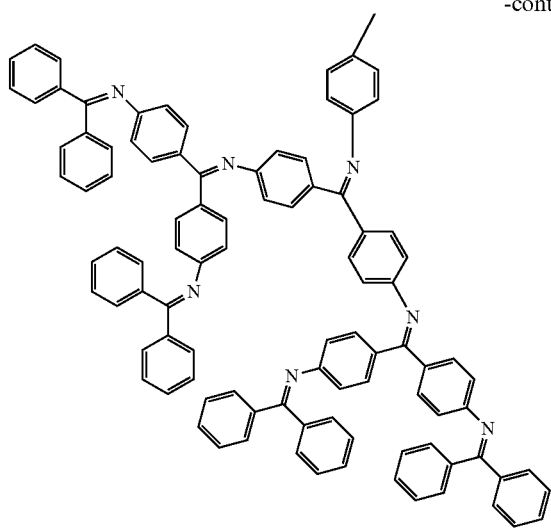
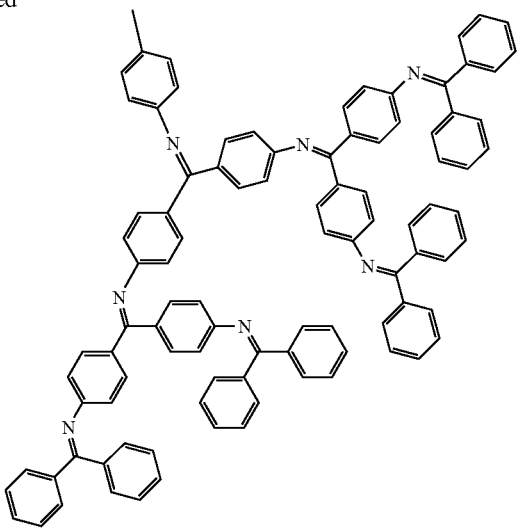

The phenyl azomethine dendrimer compound represented by the above general formula (1) is a comparatively large molecule as a single molecule compound (for example, a phenyl azomethine dendrimer compound of the 4th generation (n=3) having a diameter of about 2 nm), and possess a plurality of nitrogen atoms capable of coordinating with a metal atom within the molecule at a certain interval. Therefore, the phenyl azomethine dendrimer compound enables each atom of a plurality of metal elements to be regularly disposed one by one as a single molecule compound, within the molecule having a comparatively large size. Thus disposed a plurality of metal atoms consequently have an atomic valency of 0 by, for example, subjecting to a reduction treatment, thereby leading to formation of metal nanoparticles through binding with one another within the phenyl azomethine dendrimer.

The size of the phenyl azomethine dendrimer compound can be adjusted by appropriately selecting the generation number, the size of the aromatic group bound to a terminal, and the size of a substituent of the aromatic group bound to a terminal. The size of the dendrimer metal complex formed using a phenyl azomethine dendrimer compound can be adjusted by controlling the size of the phenyl azomethine dendrimer compound based on the structure.

In order to synthesize the phenyl azomethine dendrimer, known methods may be used. Examples of these methods include a method of reacting benzophenone with diaminobenzophenone in a chlorobenzene solvent in the presence of titanium chloride and a base and sequentially reacting the resulting solution with diaminobenzophenone to increase the generation number, but are not limited thereto.

The phenyl azomethine dendrimer compound described above is mixed with a metal compound in a solution, which allows the metal element in the metal compound to coordinate to a nitrogen atom in the phenyl azomethine dendrimer compound to form a metal complex of the phenyl azomethine dendrimer compound.

The metal element coordinating to the phenyl azomethine dendrimer compound may be any metal element that can form a metal complex with the dendrimer compound. Preferred examples of the metal element include Ga, Au, Fe, Pt, Ti, Sn, Cu, V, Ag, Ir, Tl, Ru, and Rh. These metal elements may be used in combination of two or more thereof. Preferred examples of the metal compound used for preparing the metal complex of the phenyl azomethine dendrimer compound include chlorides, bromides, and iodides of the preferred metal elements mentioned above. In addition, acetylacetonates of the above-mentioned preferred metal elements can be also used for preparing the metal complex of the phenyl azomethine dendrimer compound.

Preferred examples of the solvent for dissolving the phenyl azomethine dendrimer compound include chlorine-containing organic solvents such as dichloromethane, chloroform, 1,2-dichloroethane, 1,1-dichloroethane, and carbon tetrachloride; aromatic organic solvents such as benzene, toluene, xylene, chlorobenzene, anisole, and acetophenone; and organic solvents such as cyclohexanone, tetrahydrofuran, limonene, and propylene glycol monoethyl ether acetate.

The particle diameter of the thus-formed metal complex of the phenyl azomethine dendrimer compound is appropriately selected depending on the pore diameter of the mesoporous material, which is described below. The metal complex of the phenyl azomethine dendrimer compound preferably has a particle diameter of 2 to 6 nm. The metal complex of the phenyl azomethine dendrimer compound having such a particle diameter can be favorably supported in the pores of the mesoporous material. The particle size of a metal complex can be determined as a molecular size determined from the hydrodynamic radius measured by size exclusion chromatography (GPC/SEC).

Mesoporous Material

The mesoporous material may be any material and may have any shape. The mesoporous material is typically in a particle or a film shape. The mesoporous material is preferably silica, a metal, or a metal oxide. Examples of the metal include nickel, cobalt, palladium, copper, gold, platinum, silver, and alloys thereof. Examples of the metals of the metal oxides include Ce, Zr, Al, Ti, Mg, W, Fe, Sr, and Y. When the mesoporous material is a metal oxide, the metal oxide may contain two or more metal elements. The mesoporous material is more preferably silica, titania, zirconia, alumina, platinum, or zeolite.

The average diameter of the pores of the mesoporous material is appropriately selected depending on the size of the metal complex of the phenyl azomethine dendrimer compound. The pores of the mesoporous material preferably has an average diameter of 2 to 15 nm, more preferably 2 to 7 nm, and most preferably 2 to 5 nm, because of easiness of supporting the metal complex of the phenyl azomethine dendrimer compound in the pores while avoiding aggregation of the metal complex. The average diameter of the pores of the mesoporous material can be measured by a gas absorption method and TEM observation.

Method of Supporting Metal Complex by Mesoporous Material

As described above, a phenyl azomethine dendrimer compound can be supported in the pores of a mesoporous material by bringing a solution of the metal complex of the phenyl azomethine dendrimer compound and the mesoporous material into contact with each other. The contact of the solution of the metal complex of the phenyl azomethine dendrimer compound and the mesoporous material may be achieved by any method. In general, it is preferred to immerse the mesoporous material in the solution of the metal complex of the phenyl azomethine dendrimer compound. In such a case, the solution of the metal complex of the phenyl azomethine dendrimer compound to which the mesoporous material is added may be stirred as needed. The amount of the mesoporous material is not particularly limited and is appropriately selected considering, for example, the relative surface area and the pore volume of the mesoporous material.

The metal complex-supporting mesoporous material formed in a solution is collected from the solution by a method such as filtration and may be then dried.

Metal Complex-Supporting Mesoporous Material

The thus-produced metal complex-supporting mesoporous material supporting the metal complex of the phenyl azomethine dendrimer compound in the pores thereof is suitably used as a precursor for producing a mesoporous material supporting metal-containing nanoparticles. The metal complex-supporting mesoporous material can be suitably used, for example, as a catalyst, depending on the metal compound contained in the metal complex.

Method of Producing Mesoporous Material Supporting Metal-Containing Nanoparticles A mesoporous material supporting metal-containing nanoparticles can be produced by converting the metal complex in a metal complex-supporting mesoporous material, prepared by the method described above, into a phenyl azomethine dendrimer compound encapsulating metal-containing nanoparticles and then removing the phenyl azomethine dendrimer compound from the mesoporous material.

The metal complex may be converted into the phenyl azomethine dendrimer compound encapsulating metal-containing nanoparticles by any method, e.g., a chemical processing using chemicals or a physical processing using heat or light.

For example, in a metal complex composed of a phenyl azomethine dendrimer and $GaCl_3$, the dendrimer complex is hydrolyzed by, for example, a method of bringing the dendrimer complex into contact with hydrochloric acid vapor to generate a dendrimer containing $Ga(OH)_3$. $Ga(OH)_3$ generated in this way can be further heated to generate $Ga_2O_3$.

In a metal complex composed of a phenyl azomethine dendrimer and $PtCl_4$, $PtCl_4$ is reduced by treating the dendrimer complex with a reducing agent to form platinum nanoparticles inside the phenyl azomethine dendrimer. Examples of the reducing agent include sodium borohydride, sodium cyanoborohydride, hydrogen, hydrazines, lithium aluminum hydride, diisobutylaluminum hydride, lithium borohydride, tetra-n-butylammonium borohydride, methylammonium borohydride, lithium triethylborohydride, borane complexes, sodium triacetoxyborohydride, zinc borohydride, lithium tributylborohydride, potassium tributylborohydride, Schwartz reagent, Stryker reagent, tributyl tinhydride, sodium hydride, lithium hydride, calcium hydride, sodium benzophenone ketyl, and hydrogen peroxide.

In a metal complex composed of a phenyl azomethine dendrimer compound and $AuCl_3$, $AuCl_3$ is reduced by irradiating the dendrimer complex with light such as ultraviolet light to form gold nanoparticles inside the phenyl azomethine dendrimer. Alternatively, $AuCl_3$ is reduced by treating the dendrimer complex with a reducing agent to form gold nanoparticles inside the phenyl azomethine dendrimer. Examples of the reducing agent include sodium borohydride, sodium cyanoborohydride, hydrogen, hydrazines, lithium aluminum hydride, diisobutylaluminum hydride, lithium borohydride, tetra-n-butylammonium borohydride, methylammonium borohydride, lithium triethylborohydride, borane complexes, sodium triacetoxyborohydride, zinc borohydride, lithium tributyl borohydride, potassium tributylborohydride, Schwartz reagent, Stryker reagent, tributyl tinhydride, sodium hydride, lithium hydride, calcium hydride, sodium benzophenone ketyl, and hydrogen peroxide.

The phenyl azomethine dendrimer compound may be removed from the mesoporous material by any method. Preferred examples of the removal method include thermal decomposition such as firing and preferably oxidative decomposition such as ozone treatment.

The metal-containing nanoparticles formed in the pores of the mesoporous material may be further subjected to chemical treatment or physical treatment. For example, when the metal-containing nanoparticles are $Ga_2O_3$ nanoparticles, GaN nanoparticles can be generated by bringing the mesoporous material supporting the $Ga_2O_3$ nanoparticles into contact with a nitrogen-containing gas such as an ammonia or nitrogen gas to react the $Ga_2O_3$ nanoparticles with the nitrogen-containing compound under heating. The nitrogen-containing gas may be supplied into a reaction apparatus together with a carrier gas. Preferred examples of the carrier gas include nitrogen and argon. And argon is most preferred among those above. The heating temperature on this occasion is preferably 500 to 1200° C., more preferably 650 to 1100° C., and most preferably 750 to 1050° C. Instead of the reaction with a nitrogen-containing gas under heating, plasma ion treatment using a nitrogen gas and a hydrogen gas or radical nitridation treatment using ammonia and a hydrogen gas may be employed.

The mesoporous material supporting metal-containing nanoparticles produced as in above can be used for various purposes, for example, as a catalyst, a quantum dot, or a fluorescent material, depending on the type of the metal-containing nanoparticles.

EXAMPLES

Next, the present invention will be described in more detail by showing examples. However, the present invention is not limited to the following examples.

In the following examples, DPAG4er having the following structure was used as the phenyl azomethine dendrimer compound.

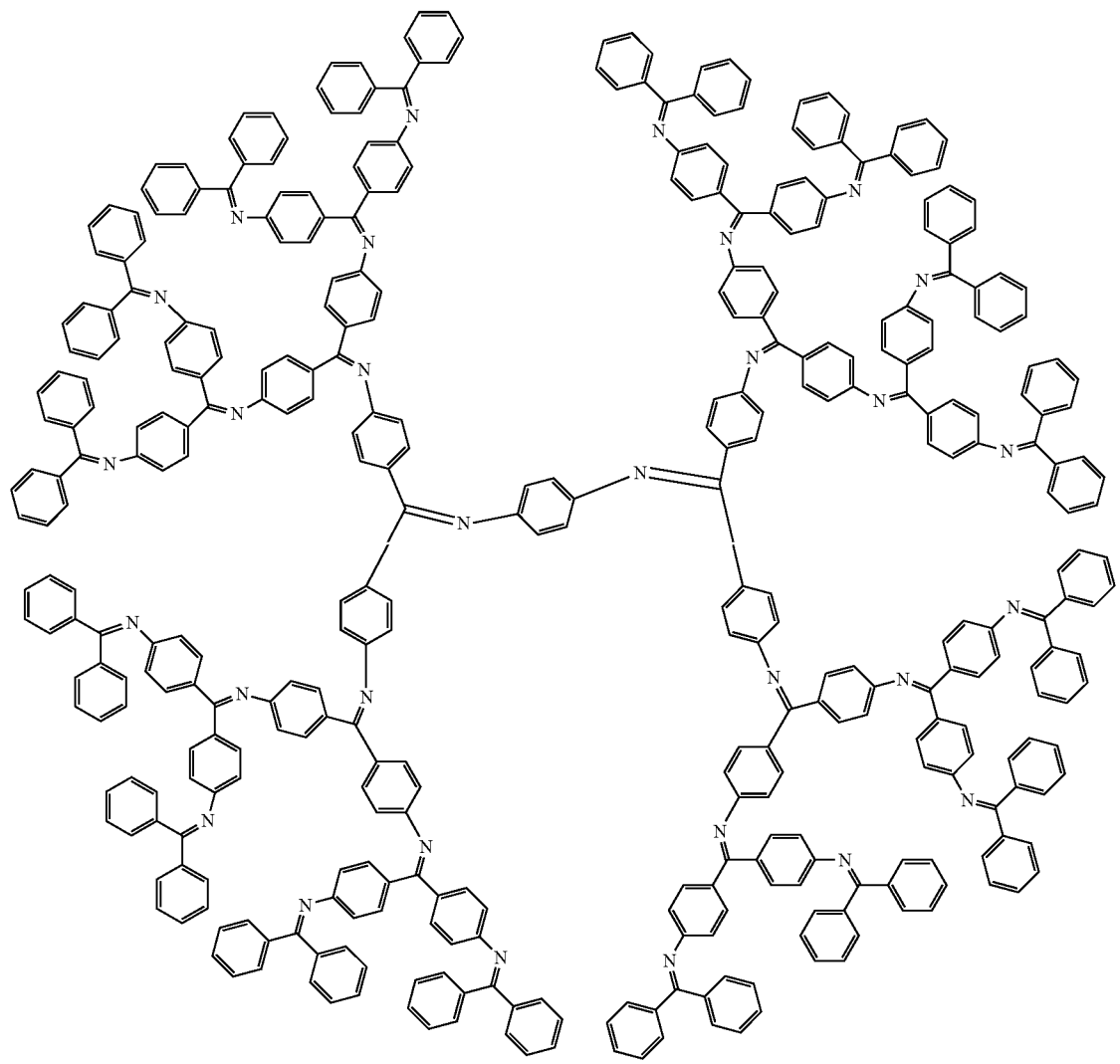

Example 1

DPAG4er (5 µmol/L) was dissolved in a solvent mixture of chloroform and acetonitrile (volume ratio: 1:1). To this solution (3 mL) was added a solution (150 µL) of 4.68 mmol/L $AuCl_3$ in acetonitrile to prepare a solution of 5 µmol/L DPAG4er-$AuCl_3$ complex. The equivalent amount of $AuCl_3$ to DPAG4er is 14 equivalents. The equivalent amount of $AuCl_3$ means the number of moles of $AuCl_3$ per 1 mol of DPAG4er. Mesoporous silica (MCM-41, pore diameter: 2 to 3 nm, 20 mg) was added to the resulting solution of the DPAG4er-$AuCl_3$ complex so that the DPAG4er-$AuCl_3$ complex is supported by mesoporous silica.

The light absorption spectra of the solution of the DPAG4er-$AuCl_3$ complex and the solution of the DPAG4er-$AuCl_3$ complex to which mesoporous silica was added were measured in a wavelength range of 300 to 500 nm. FIG. 1 shows the absorption spectrum (a) of the solution of the DPAG4er-$AuCl_3$ complex to which mesoporous silica was added and the absorption spectrum (b) of the solution of the DPAG4er-$AuCl_3$ complex. FIG. 1 demonstrates that the absorption disappears by adding mesoporous silica to the solution of the DPAG4er-$AuCl_3$ complex. This means that in the solution of the DPAG4er-$AuCl_3$ complex to which mesoporous silica was added, the DPAG4er-$AuCl_3$ complex is supported by mesoporous silica.

The solution of the DPAG4er-$AuCl_3$ complex to which mesoporous silica was added was dried into a powder of mesoporous silica supporting the DPAG4er-$AuCl_3$ complex. The resulting powder was irradiated with ultraviolet rays to prepare mesoporous silica supporting DPAG4er encapsulating Au nanoparticles.

Figure 2:
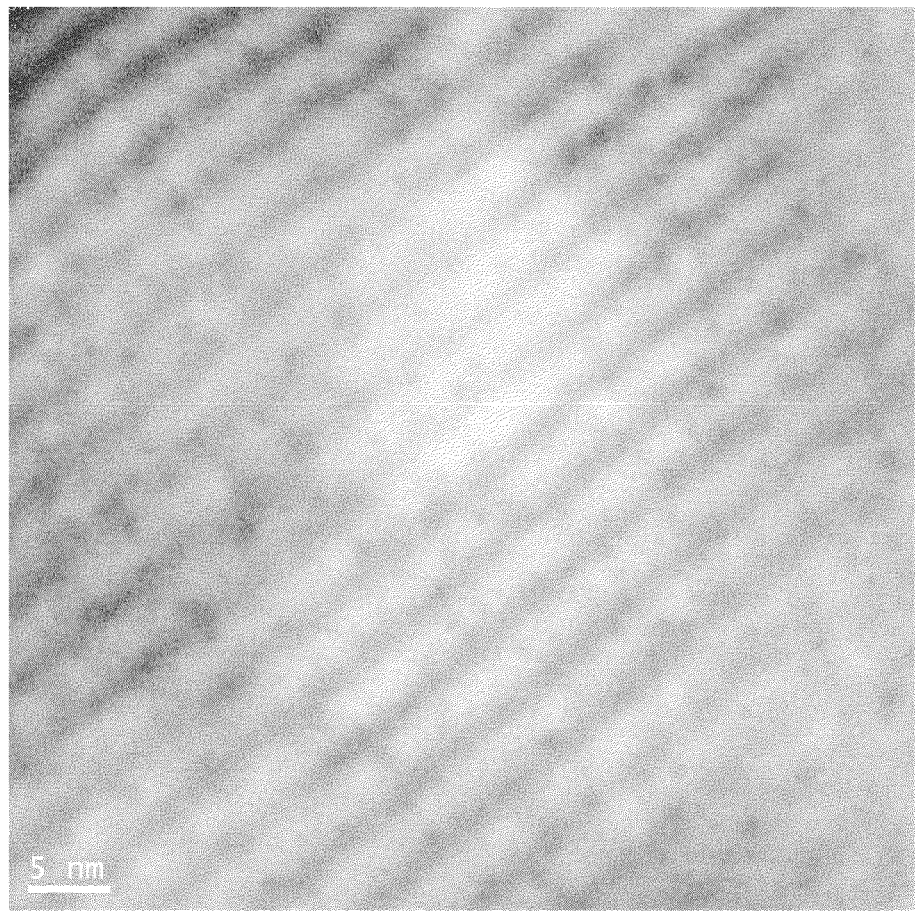
FIG. 2 is a scanning transmission electron microscopic image of mesoporous silica supporting DPAG4er encapsulating Au nanoparticles in a state of being dispersed on a TEM grid, prepared in Example 1.

The powder irradiated with ultraviolet rays was dispersed in a solvent mixture of chloroform and acetonitrile with a volume ratio of 1:1. The resulting dispersion was cast onto a polymer-supporting carbon mesh TEM grid, and the surface of the TEM grid was observed with a scanning transmission electron microscope (HAADF-STEM, JEM-2100F, manufactured by JEOL Ltd.). FIG. 2 shows an image of the surface of the TEM grid observed by HAADF-STEM. In FIG. 2, minute black spots of Au nanoparticles are observed, which demonstrates that DPAG4er encapsulating Au nanoparticles is supported by mesoporous silica.

Figure 3:
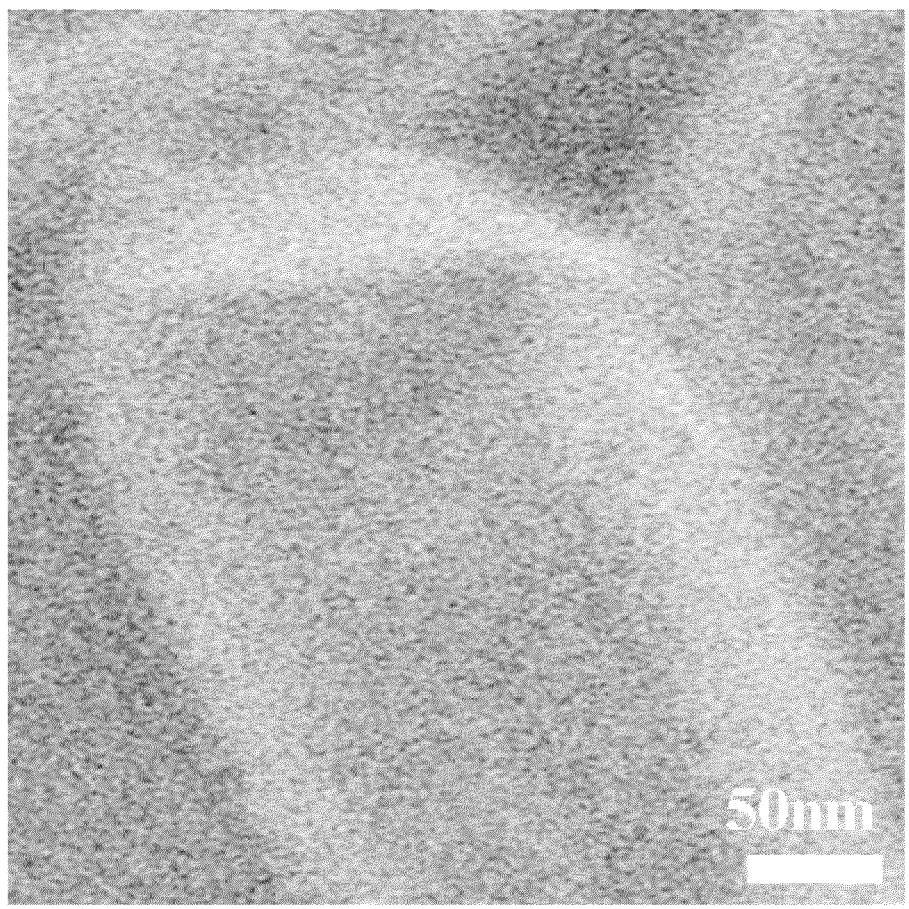
FIG. 3 is a scanning electron microscopic image of mesoporous silica (MCM-41) supporting DPAG4er encapsulating Au nanoparticles, prepared in Example 1.
Figure 4:
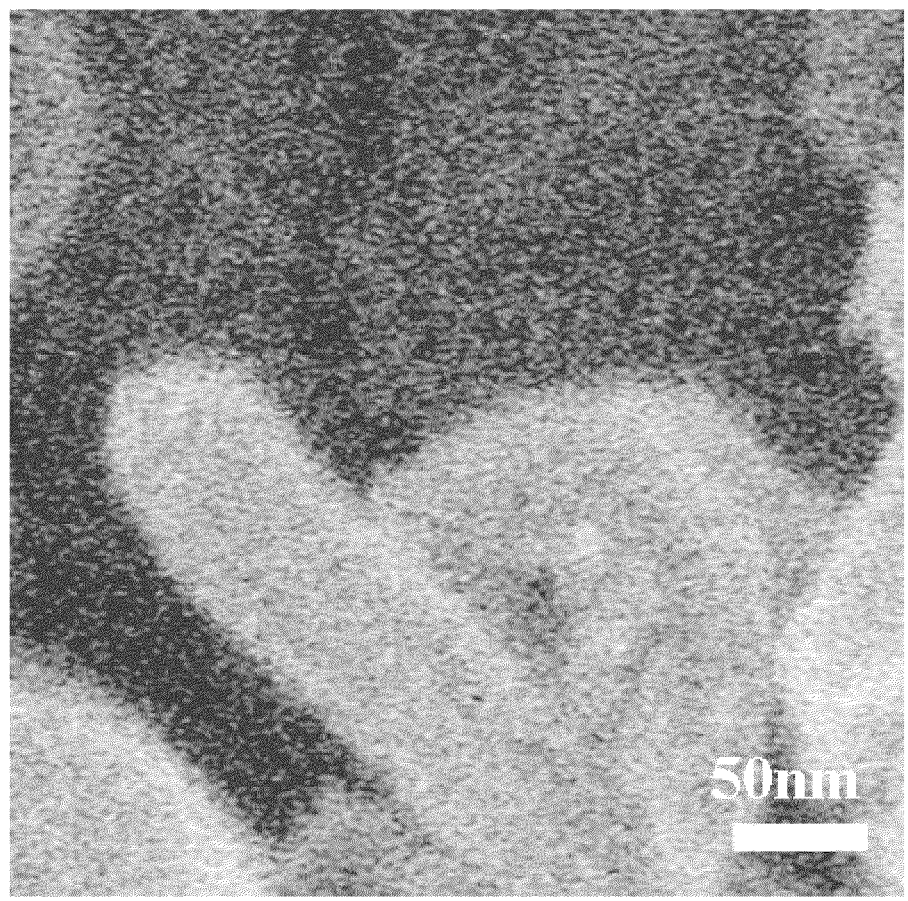
FIG. 4 is a scanning electron microscopic image of mesoporous silica (MCM-41).

FIG. 3 shows an image of the powder irradiated with ultraviolet rays observed with a scanning electron microscope (SEM, SU8000, manufactured by Hitachi High-Tech Solutions Corporation). FIG. 4 shows an image of mesoporous silica (SBA-15) observed with an SEM.

In SEM, secondary electrons generated by irradiation of a sample with electron rays are observed. Accordingly, in observation of an insulating sample with an SEM, the image of the insulating sample is whitely relieved due to loss of electrons from the sample surface, i.e., a "charge-up" phenomenon occurs. Such charge-up is observed in the image of FIG. 3, whereas no charge-up is observed in the image of FIG. 4. This demonstrates that in the powder irradiated with ultraviolet rays, DPAG4er encapsulating Au nanoparticles is dispersed in the pores of mesoporous silica.

The resulting mesoporous silica supporting DPAG4er encapsulating Au nanoparticles is subjected to heat treatment or oxidation treatment using, for example, ozone to remove DPAG4er. As a result, mesoporous silica supporting the Au nanoparticles in its pores is given.

Example 2

DPAG4er (5 μmol/L) was dissolved in a solvent mixture of chloroform and acetonitrile (volume ratio: 1:1). To this solution (3 mL) was added a solution (150 μL) of 4.68 mmol/L $AuCl_3$ in acetonitrile to prepare a solution of 5 μmol/L DPAG4er-$AuCl_3$ complex. The equivalent amount of $AuCl_3$ to DPAG4er is 14 equivalents. The equivalent amount of $AuCl_3$ means the number of moles of $AuCl_3$ per 1 mol of DPAG4er. Mesoporous silica (SBA-15, pore diameter: 5 to 7 nm, 5 mg) was added to the resulting solution of the DPAG4er-$AuCl_3$ complex so that the DPAG4er-$AuCl_3$ complex is supported by mesoporous silica.

Figure 5:
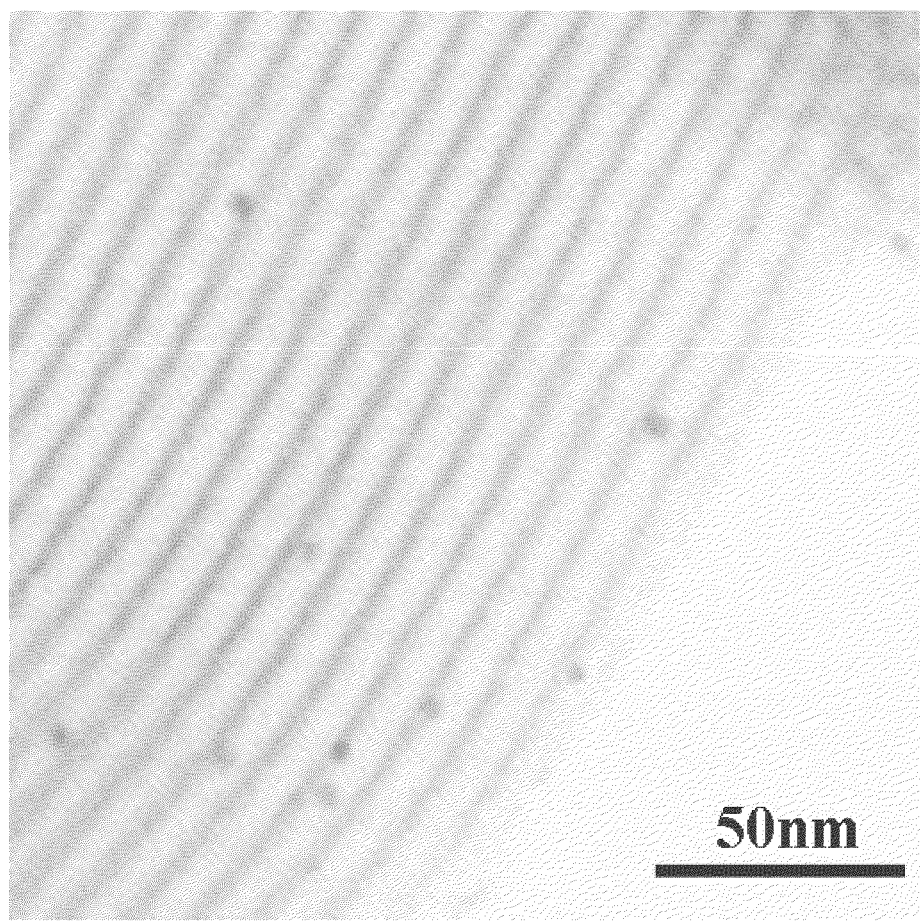
FIG. 5 is a scanning transmission electron microscopic image of mesoporous silica supporting DPAG4er encapsulating Au nanoparticles in a state of being dispersed on a TEM grid, prepared in Example 2.

Subsequently, mesoporous silica supporting DPAG4er encapsulating Au nanoparticles was prepared as in Example 1. The resulting mesoporous silica supporting DPAG4er encapsulating Au nanoparticles was cast onto a polymer-supporting carbon mesh TEM grid as in Example 1. FIG. 5 shows an image of the TEM grid surface observed by HAADF-STEM as in Example 1. In FIG. 5, minute black spots of Au nanoparticles are observed, which demonstrates that DPAG4er encapsulating Au nanoparticles is supported by mesoporous silica.

Example 3

DPAG4er (5 μmol/L) was dissolved in a solvent mixture of chloroform and acetonitrile (volume ratio: 1:1). To this solution (3 mL) was added a solution (120 μL) of 3 mol/L $GaCl_3$ in acetonitrile to prepare a solution of 5 μmol/L DPAG4er-$GaCl_3$ complex. The equivalent amount of $GaCl_3$ to DPAG4er is 14 equivalents. The equivalent amount of $GaCl_3$ means the number of moles of $GaCl_3$ per 1 mol of DPAG4er. Mesoporous silica (MCM-41, pore diameter: 2 to 3 nm, 5.0 mg) was added to the resulting solution (3 mL) of the DPAG4er-$GaCl_3$ complex so that the DPAG4er-$GaCl_3$ complex is supported by mesoporous silica. The light absorption spectra of the solution of the DPAG4er-$GaCl_3$ complex and the solution to which mesoporous silica was added were measured in a wavelength range of 300 to 600 nm. The results demonstrate that the peak derived from DPAG4er-$GaCl_3$ complex, which is observed in the spectrum of the solution of DPAG4er-$GaCl_3$ complex, disappears in the spectrum of the solution containing mesoporous silica. This demonstrates that in the solution to which mesoporous silica was added, the DPAG4er-$GaCl_3$ complex is supported by mesoporous silica.

The solid content was collected from the solution containing mesoporous silica supporting the DPAG4er-$GaCl_3$ complex by filtration. The collected powder was sufficiently dried to give a yellow powder of mesoporous silica supporting the DPAG4er-$GaCl_3$ complex. The resulting powder was exposed to an atmosphere of hydrochloric acid (10% by mass) for 1 hour to hydrolyze $GaCl_3$ in the DPAG4er-$GaCl_3$ complex to generate $Ga(OH)_3$. Subsequently, the powder was heated at 100° C. for 1 hour to convert $Ga(OH)_3$ into $Ga_2O_3$. The powder was then treated with ozone to remove organic substances in the powder to give a white powder.

Figure 6:
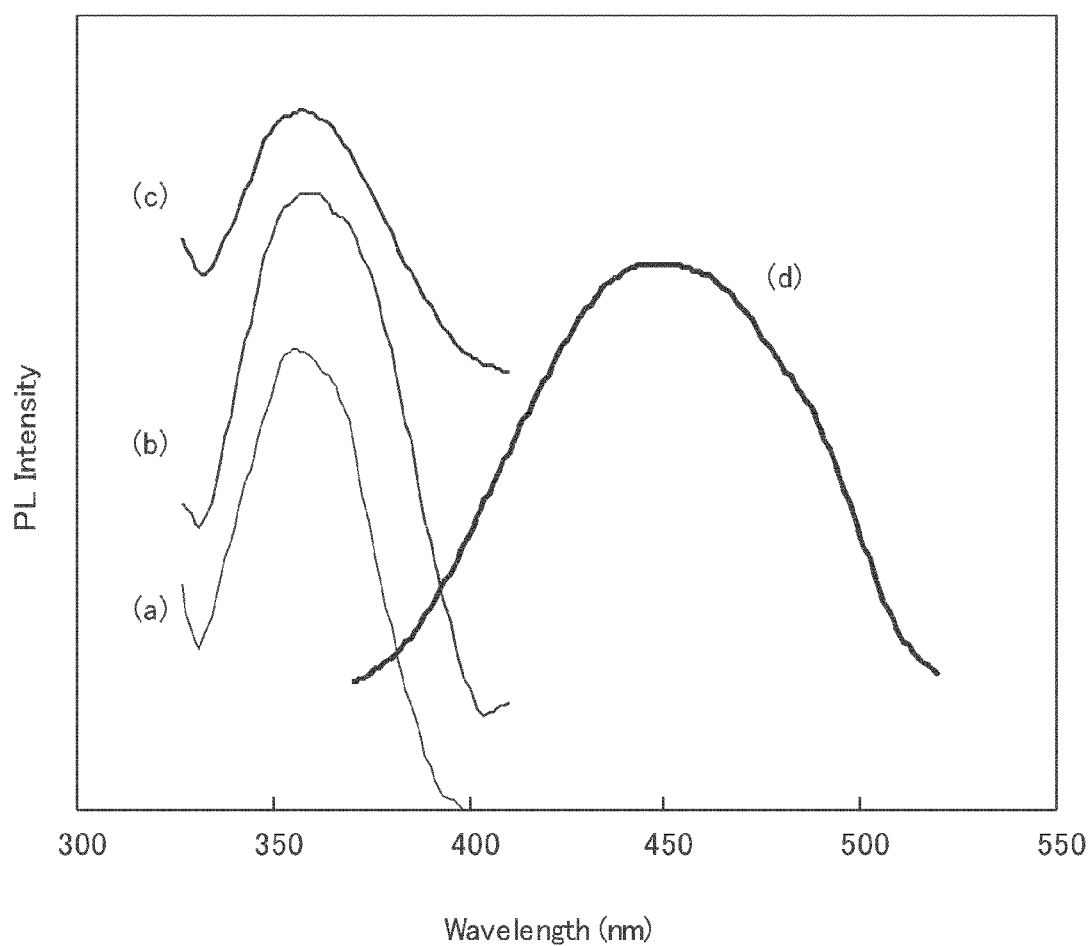
FIG. 6 is a graph showing fluorescence spectra of mesoporous silica supporting $Ga_2O_3$ nanoparticles prepared in Example 3 and commercially available $Ga_2O_3$ particles.

The fluorescence spectrum of the resulting white powder was measured in a wavelength range of 300 to 550 nm with a spectrofluorometer (FP-8300, manufactured by JASCO Corporation) at an excitation wavelength of 230 nm. In addition, the fluorescence spectra of mesoporous silica supporting $Ga_2O_3$ prepared by heat treatment at 300° C. or 500° C. instead of 100° C. and the fluorescence spectrum of a commercially available $Ga_2O_3$ powder (manufactured by Wako Pure Chemical Industries, Ltd.) were measured. FIG. 6 shows the fluorescence spectra of these samples. FIG. 6 shows the fluorescence spectrum (a) of the sample prepared by heat treatment at 100° C., the fluorescence spectrum (b) of the sample prepared by heat treatment at 300° C., the fluorescence spectrum (c) of the sample prepared by heat treatment at 500° C., and the fluorescence spectrum (d) of the commercially available $Ga_2O_3$ powder.

The spectra (a) to (c) in FIG. 6 demonstrate that the peaks of $Ga_2O_3$ prepared from mesoporous silica supporting the DPAG4er-$GaCl_3$ complex largely shift to the shorter wavelength side than the peak of the commercially available $Ga_2O_3$ powder. This shift in peak suggests occurrence of any defect in the crystal structure of the $Ga_2O_3$ nanoparticles supported by mesoporous silica. The spectra (a) to (c) in FIG. 6 demonstrate that the fluorescence spectral shape of $Ga_2O_3$ prepared from mesoporous silica supporting the DPAG4er-$GaCl_3$ complex does not change by influence of the temperature of the heat treatment in preparation of $Ga_2O_3$.

What is claimed is:

1. A method of producing a metal complex-supporting mesoporous material, comprising:
bringing a solution containing a metal complex of a phenyl azomethine dendrimer compound represented by Formula (1) coordinated with a metal element into contact with a mesoporous material:

$$AB_nR_m \quad (1)$$

wherein A in the above general formula (1) is a core molecular group of the phenyl azomethine dendrimer and represented by a structure of the following formula:

wherein $R^1$ represents an aromatic group that may have a substituent, and p represents the number of bonds to the $R^1$; and B in the above general formula (1) is represented by a structure of the following formula:

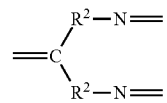

in which one azomethine bond is formed for the A, the $R^2$ represents an aromatic group that may have the same or different substituent;

R in the above general formula (1) is represented by a structure of the following formula:

in which an azomethine bond is formed to the B as a terminal group, and the $R^3$ represents an aromatic group that may have the same or different substituent;

n represents a generation number through a structure of the B of the phenyl azomethine dendrimer; and m represents the number of terminal groups R of the phenyl azomethine dendrimer, and m is equal to p provided that n is 0, whereas m is equal to $2^n p$ provided that n is no less than 1.

2. The method of producing a metal complex-supporting mesoporous material according to claim 1, wherein the metal element is at least one selected from the group consisting of Ga, Au, Fe, Pt, Ti, Sn, Cu, V, Ag, Ir, Tl, Ru, and Rh.

3. The method of producing a metal complex-supporting mesoporous material according to claim 1, wherein the mesoporous material has pores having an average diameter of 2 to 7 μm.

4. A metal complex-supporting mesoporous material supporting a metal complex of a phenyl azomethine dendrimer compound represented by Formula (1) coordinated with a metal element:

$$AB_n R_m \qquad (1)$$

wherein A in the above general formula (1) is a core molecular group of the phenyl azomethine dendrimer and represented by a structure of the following formula:

wherein $R^1$ represents an aromatic group that may have a substituent, and p represents the number of bonds to the $R^1$; and B in the above general formula (1) is represented by a structure of the following formula:

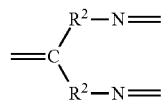

in which one azomethine bond is formed for the A, the $R^2$ represents an aromatic group that may have the same or different substituent;

R in the above general formula (1) is represented by a structure of the following formula:

in which an azomethine bond is formed to the B as a terminal group, and the $R^3$ represents an aromatic group that may have the same or different substituent;

n represents a generation number through a structure of the B of the phenyl azomethine dendrimer; and m represents the number of terminal groups R of the phenyl azomethine dendrimer, and m is equal to p provided that n is 0, whereas m is equal to $2^n p$ provided that n is no less than 1.

5. The metal complex-supporting mesoporous material according to claim 4, wherein the metal element is at least one selected from the group consisting of Ga, Au, Fe, Pt, Ti, Sn, Cu, V, Ag, Ir, Tl, Ru, and Rh.

6. The metal complex-supporting mesoporous material according to claim 4, wherein the mesoporous material has pores having an average diameter of 2 to 7 μm.

7. A method of producing a mesoporous material supporting metal-containing nanoparticles, comprising:

converting a metal complex in a metal complex-supporting mesoporous material according to claim 4 into a phenyl azomethine dendrimer compound encapsulating metal-containing nanoparticles; and then removing the phenyl azomethine dendrimer compound from the mesoporous material.

* * * * *